US010055860B2

United States Patent
Shi et al.

(10) Patent No.: US 10,055,860 B2
(45) Date of Patent: Aug. 21, 2018

(54) COMPUTED TOMOGRAPHY APPARATUS AND EMPIRICAL PRE-WEIGHTING METHOD FOR DECREASING IMAGE NOISE NONUNIFORMITY

(71) Applicant: TOSHIBA MEDICAL SYSTEMS CORPORATION, Otawara (JP)

(72) Inventors: Daxin Shi, Buffalo Grove, IL (US); Yu Zou, Naperville, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 15/167,521

(22) Filed: May 27, 2016

(65) Prior Publication Data

US 2017/0345190 A1    Nov. 30, 2017

(51) Int. Cl.
| | |
|---|---|
| G06K 9/00 | (2006.01) |
| A61B 6/00 | (2006.01) |
| G06T 11/00 | (2006.01) |
| G06T 7/40 | (2017.01) |
| G06T 5/00 | (2006.01) |
| A61B 6/03 | (2006.01) |

(52) U.S. Cl.
CPC .......... *G06T 11/006* (2013.01); *A61B 6/5205* (2013.01); *G06T 5/002* (2013.01);
(Continued)

(58) Field of Classification Search
USPC ....... 382/100, 103, 107, 128–134, 154, 162, 382/168, 173, 181, 199, 209, 224, 232,
(Continued)

(56) References Cited

U.S. PATENT DOCUMENTS

| | | | |
|---|---|---|---|
| 2003/0076988 A1* | 4/2003 | Liang | G06T 5/10 382/131 |
| 2009/0232269 A1 | 9/2009 | Hsieh et al. | |

(Continued)

OTHER PUBLICATIONS

Jing Wang, et al., Penalized Weighted Least-Squares Approach to Sinogram Noise Reduction and Image Reconstruction for Low-Dose X-Ray Computed Tomography, Oct. 2006, 17 pages.
(Continued)

*Primary Examiner* — Seyed Azarian
(74) *Attorney, Agent, or Firm* — Oblon, McClelland, Maier & Neustadt, L.L.P.

(57) ABSTRACT

A computed tomography (CT) method and apparatus including a radiation source configured to produce radiation directed to an object space, and a plurality of detector elements configured to detect the radiation produced from the radiation source through the object space and generate projection data. A rotation mount is configured to rotate the radiation source around the object space. Processing circuitry is configured to cause the rotation mount to rotate the radiation source, and to receive the projection data. The projection data includes a plurality of projection data sets. The processing circuitry calculates a set of weights based on the projection data sets, calculates a set of pre-weights based on the weights, and minimizes a penalized weighted least-squares cost function to produce a reconstructed image. The cost function is a sum of a weighted least-squares term, weighted using the weights, and a penalty term weighted using the pre-weights.

15 Claims, 4 Drawing Sheets

(52) U.S. Cl.
CPC .............. *G06T 7/404* (2013.01); *A61B 6/032* (2013.01); *G06T 2207/10081* (2013.01); *G06T 2207/20056* (2013.01); *G06T 2207/20182* (2013.01); *G06T 2211/421* (2013.01)

(58) Field of Classification Search
USPC ........ 382/254, 260, 274–276, 286–291, 305, 382/312; 378/4, 19, 21
See application file for complete search history.

(56) References Cited

U.S. PATENT DOCUMENTS

| | | | | |
|---|---|---|---|---|
| 2011/0286651 | A1* | 11/2011 | Yu ........................ | G06T 11/005 382/131 |
| 2013/0202079 | A1* | 8/2013 | Yu ........................ | A61B 6/5258 378/19 |
| 2014/0219529 | A1 | 8/2014 | Shi | |
| 2014/0369463 | A1* | 12/2014 | Thibault .............. | G01N 23/046 378/19 |
| 2014/0369580 | A1* | 12/2014 | Yu ........................ | G06T 11/006 382/131 |
| 2015/0030227 | A1 | 1/2015 | Liang et al. | |

OTHER PUBLICATIONS

Jing Wang, et al., Multiscale Penalized Weighted Least-Squares Sinogram Restoration for Low-Dose X-Ray Computed Tomography, 2006, 16 pages.

* cited by examiner

COMPUTED TOMOGRAPHY APPARATUS AND EMPIRICAL PRE-WEIGHTING METHOD FOR DECREASING IMAGE NOISE NONUNIFORMITY

BACKGROUND

Field

This disclosure is related to computed tomography (CT) image reconstruction of X-ray projection data obtain using a CT scanner, and more particularly relates to decreasing image noise nonuniformity in penalized weighted least squares (PWLS) approaches to CT image reconstruction.

Discussion of the Background

Computed tomography systems and methods are widely used, particularly for medical imaging and diagnosis. CT systems generally create images of one or more sectional slices through a subject's body. A radiation source, such as an X-ray source, irradiates the body from one side. A collimator, generally adjacent to the X-ray source, limits the angular extent of the X-ray beam, so that radiation impinging on the body is substantially confined to a cone-beam/fan-beam region (i.e., an X-ray projection volume) defining an image volume of the body. At least one detector (and generally many more than one detector) on the opposite side of the body receives radiation transmitted through the body substantially in the projection volume. The attenuation of the radiation that has passed through the body is measured by processing electrical signals received from the detector.

Conventional approaches to image reconstruction include filtered back-projection (FBP), iterative reconstruction methods (e.g., the algebraic reconstruction technique (ART) method and the total variation minimization regularization method), Fourier-transform-based methods (e.g., the direct Fourier method), and statistical methods (e.g., maximum-likelihood expectation-maximization algorithm based methods).

BRIEF DESCRIPTION OF THE DRAWINGS

A more complete appreciation of the disclosed embodiments and many of the attendant advantages thereof will be more readily obtained by reference to the accompanying drawings when considered in connection with following detailed description, wherein.

DETAILED DESCRIPTION

Figure 1:
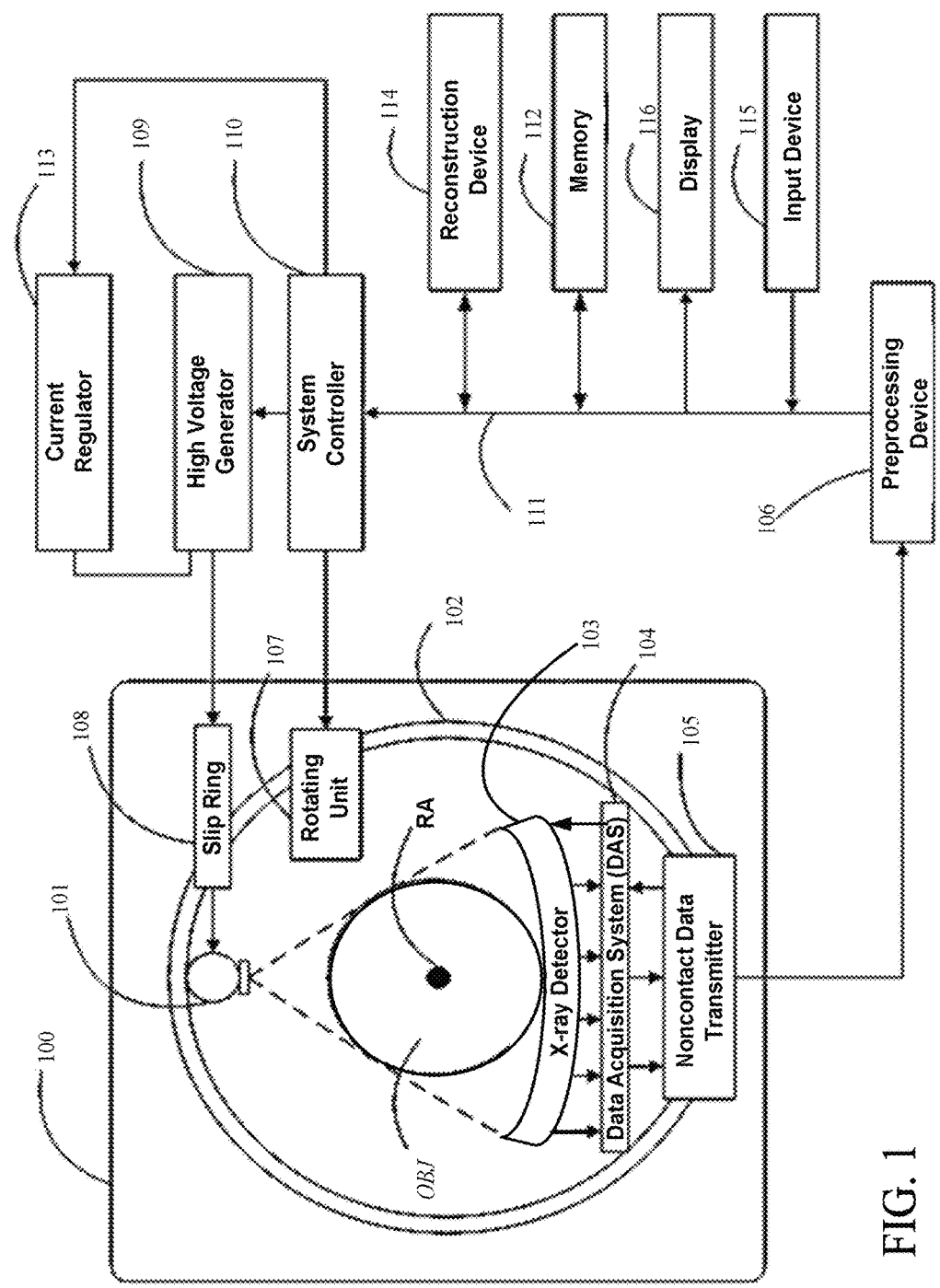
FIG. 1 illustrates a schematic of an implementation of a computed tomography scanner.

The following descriptions are meant to further clarify the present disclosure by giving specific examples and embodiments of the disclosure. These embodiments are meant to be illustrative rather than exhaustive. The full scope of the disclosure is not limited to any particular embodiment disclosed in this specification, but rather is defined by the claims.

In one embodiment of the present disclosure, the reconstruction uses a penalized weighted least-squares approach. In a penalized weighted least-squares approach, the reconstruction is achieved by minimizing a cost function. The cost function is a sum of a two terms, a weighted least-squares term and a penalty term or regulator term. The cost function is given by $$C(f) = \frac{1}{2}(Af - g)^T * W * (Af - g) + \beta \sum_i u_i(f_i)$$

where f is the three-dimensional volume image to be reconstructed, g is a two-dimensional projection data image, A is the system matrix or forward projection operator, $^T$ indicates a transpose, W is a weighting matrix containing statistical information on the projection data, $\beta$ is a regularization or penalty parameter, $f_i$ is the value of the image f at the $i^{th}$ voxel, $\Sigma_i u_i(f_i)$ is a regularizer or penalty function defined for each voxel $f_i$, and C(f) is the cost function evaluated for the image f.

In the expression for the cost function C above, the images f and g can be represented by column vectors; the forward projection operator A and the weighting matrix W are then represented by matrices. The regularizer term is a voxel-by-voxel sum of the regularizer function evaluated over the voxels of the image f.

The system of equations Af=g is overdetermined, i.e., there are more projection images g captured than are required to solve for the image f. The value off that minimizes the cost function C can be solved for using many different optimization algorithms known to one of ordinary skill in the art, for example, the gradient descent algorithm, the Gauss-Seidel algorithm, and the like.

The weighting matrix W contains statistical information about the projection data. The weighting matrix is a square matrix with a number of rows, and a number of columns equal to a number of pixels in a projected image g. In one example, the weighting matrix W can be the inverse of the covariance matrix of the pixels in the set of projected images. In another example, a weighting matrix W for an uncorrelated system is a diagonal matrix, $$W = \begin{pmatrix} w_1 & \cdots & 0 \\ \vdots & \ddots & \vdots \\ 0 & \cdots & w_N \end{pmatrix}$$

with the statistical information along the diagonal being the reciprocal of the variance $$w_i = 1/\sigma_i^2$$

for the corresponding pixel over the set of projected images.

In the cost function, the least-squares term generally encourages agreement with the measured projection data. The weighting matrix W suppresses the contribution to the total error of the terms having a larger variance relative to the terms having a smaller variance.

Many regularizer terms have been proposed for image reconstruction. These regularizer terms are generally constructed to discourage features that are not desired in the reconstructed image. For example, the regularization term can discourage disparities between neighboring pixel values in the reconstructed image, thereby smoothing the reconstructed image. The regularizer functions $u_i$ are local functions of the voxels, each $u_i$ taking non-zero values only for voxels within a neighborhood of the $i^{th}$ voxel. For example, $$u_i = \tfrac{1}{2} \Sigma_{k \in N_j} \rho_{jk}^{1/2} (f_j - f_k)^2$$

where $N_j$ is the set of the neighboring voxels of the $i^{th}$ voxel, and the $\rho_{jk}$ coefficients take a value of the reciprocal of the distance between the centers of the voxels, i.e., 1, $1/\sqrt{2}$, or $1/\sqrt{3}$, depending on the neighboring voxel. The regularization parameter β can be used to tune the strength of the regularizer term relative to the least squares term.

However, the image reconstructed from the projection images can suffer from image noise non-uniformity, i.e., for a uniform image, the noise is not distributed uniformly. An object being imaged that has uniform density might naively be expected to have a uniform noise distribution, but images reconstructed via PWLS can show a substantial spatial variation in the noise pattern. The non-uniform distribution of noise is undesirable, and can be mistaken for a property of the image rather than an artifact caused by the reconstruction process.

Further, this problem appears in many fields related to computed tomography that use a PWLS approach to determine a reconstructed image from projected images, such as conventional CT, single-photon emission CT (SPECT), positron emission tomography (PET), fluoroscopy, angiography, etc.

One embodiment is drawn to a method for tomographic image reconstruction including acquiring a plurality of projection data sets, calculating a set of weights based on the projection data sets, calculating a set of pre-weights based on the weights, and minimizing a penalized weighted least-squares cost function to produce a reconstructed image. The cost function is a sum of a weighted least-squares term and a penalty term. The weighted least-squares term is weighted using the calculated set of weights, and the penalty term is weighted using the calculated set of pre-weights.

Another embodiment is drawn to a method for tomographic image reconstruction including acquiring a plurality of projection data sets, calculating a set of weights based on the projection data sets, calculating a set of pre-weights based on the projection data sets, and minimizing a penalized weighted least-squares cost function to produce a reconstructed image. The cost function is a sum of a weighted least-squares term and a penalty term. The weighted least-squares term is weighted using the calculated set of weights. The penalty term is weighted using the calculated set of pre-weights.

Another embodiment is drawn to a computed tomography (CT) apparatus including a radiation source configured to produce radiation directed to an object space, and a plurality of detector elements configured to detect the radiation produced from the radiation source through the object space. The plurality of detector elements is configured to generate projection data. A rotation mount is configured to rotate the radiation source around the object space, with the radiation source being fixedly connected to the rotation mount.

Processing circuitry is configured to cause the rotation mount to rotate the radiation source around the object space, and to receive projection data from the plurality of detector elements. The projection data includes a plurality of projection data sets. The processing circuitry calculates a set of weights based on the projection data sets, calculates a set of pre-weights based on the weights, and minimizes a penalized weighted least-squares cost function to produce a reconstructed image. The cost function is a sum of a weighted least-squares term and a penalty term. The weighted least-squares term is weighted using the calculated set of weights. The sum in the penalty term is weighted using the calculated set of pre-weights.

Referring now to the drawings, wherein like reference numerals designate identical or corresponding parts throughout the several views, FIG. 1 illustrates an implementation of the radiography gantry included in a CT apparatus or scanner. As shown in FIG. 1, a radiography gantry 100 is illustrated from a side view and further includes an X-ray tube 101, an annular frame 102, and a multi-row or two-dimensional-array-type X-ray detector 103. The X-ray tube 101 and X-ray detector 103 are diametrically mounted across an object OBJ on the annular frame 102, which is rotatably supported around a rotation axis RA. A rotating unit 107 rotates the annular frame 102 at a high speed, such as 0.4 sec/rotation, while the object OBJ is being moved along the axis RA into or out of the illustrated page.

An embodiment of an X-ray computed tomography apparatus according to the present disclosure will be described below with reference to the views of the accompanying drawings. Note that X-ray computed tomography apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present disclosure can be applied to either type. In this case, the rotate/rotate type, which is currently the mainstream, will be exemplified.

The X-ray CT apparatus further includes a high voltage generator 109 that generates a tube voltage applied to the X-ray tube 101 through a slip ring 108 so that the X-ray tube 101 generates X-rays. The X-rays are emitted towards the object OBJ, whose cross-sectional area is represented by a circle. The X-ray detector 103 is located at an opposite side from the X-ray tube 101 across the object OBJ for detecting the emitted X-rays that are transmitted through the object OBJ. The X-ray detector 103 further includes individual detector elements or units. A projection image is a single two-dimensional image captured by the X-ray detector 103, and has a dimensionality of the number of individual detector elements, or pixels, of the X-ray detector 103.

The CT apparatus further includes other devices for processing the detected signals from X-ray detector 103. A data acquisition circuit or a Data Acquisition System (DAS) 104 converts a signal output from the X-ray detector 103 for each channel into a voltage signal, amplifies the signal, and further converts the signal into a digital signal. The X-ray detector 103 and the DAS 104 are configured to handle a predetermined total number of projections per rotation (TPPR). Examples of TPPRs include, but are not limited to 900 TPPR, 900-1800 TPPR, and 900-3600 TPPR.

The above-described data is sent to a preprocessing device 106, which is housed in a console outside the radiography gantry 100 through a non-contact data transmitter 105. The preprocessing device 106 performs certain corrections, such as sensitivity correction on the raw data. A memory 112 stores the resultant data, which is also called projection data at a stage before reconstruction processing. The memory 112 is connected to a system controller 110 through a data/control bus 111, together with a reconstruction device 114, input device 115, and display 116. The system controller 110 controls a current regulator 113 that limits the current to a level sufficient for driving the CT system.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 101 and the X-ray detector 103 are diametrically mounted on the annular frame 102 and are rotated around the object OBJ as the annular frame 102 is rotated about the rotation axis RA. In the fourth-generation geometry system, the detectors are fixedly placed around the patient and an X-ray tube rotates around the patient. In an alternative embodiment, the radiography gantry 100 has multiple detectors arranged on the annular frame 102, which is supported by a C-arm and a stand.

The memory 112 can store measurement values representative of the irradiance of the X-rays at the X-ray detector 103. Further, the memory 112 can store a dedicated program for executing the CT image reconstruction methods.

The pre-reconstruction processing of the projection data performed by the preprocessing device 106 can include correcting for detector calibrations, detector nonlinearities, polar effects, noise balancing, and material decomposition.

After obtaining CT projection data, the CT imaging system using the reconstruction device 114 will perform image reconstruction using the projection data. The reconstruction device 114 can execute the CT image reconstruction using various methods. Post-reconstruction processing performed by the reconstruction device 114 can include filtering and smoothing the image, volume rendering processing, and image difference processing as needed. The reconstruction device 114 can use the memory to store, e.g., projection data, reconstructed images, calibration data and parameters, and computer programs.

The reconstruction device 114 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 112 can be non-volatile, such as ROM, EPROM, EEPROM or FLASH memory. The memory 112 can also be volatile, such as static or dynamic RAM, and a processor (processing circuitry), such as a microcontroller or microprocessor, can be provided to manage the electronic memory as well as the interaction between the FPGA or CPLD and the memory.

Alternatively, the CPU in the reconstruction device 114 can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 116. The display 116 can be an LCD display, CRT display, plasma display, OLED, LED, or any other display known in the art.

The memory 112 can be a hard disk drive, CD-ROM drive, DVD drive, FLASH drive, RAM, ROM, or any other electronic storage known in the art.

The method of the present disclosure uses pre-weighting factors $B_i$ in the regularization term of the cost function C $$C(f) = \frac{1}{2}(Af-g)^T * W * (Af-g) + \beta \sum_i B_i u_i(f_i)$$

in order to decrease the noise nonuniformity of the image.

Figure 2:
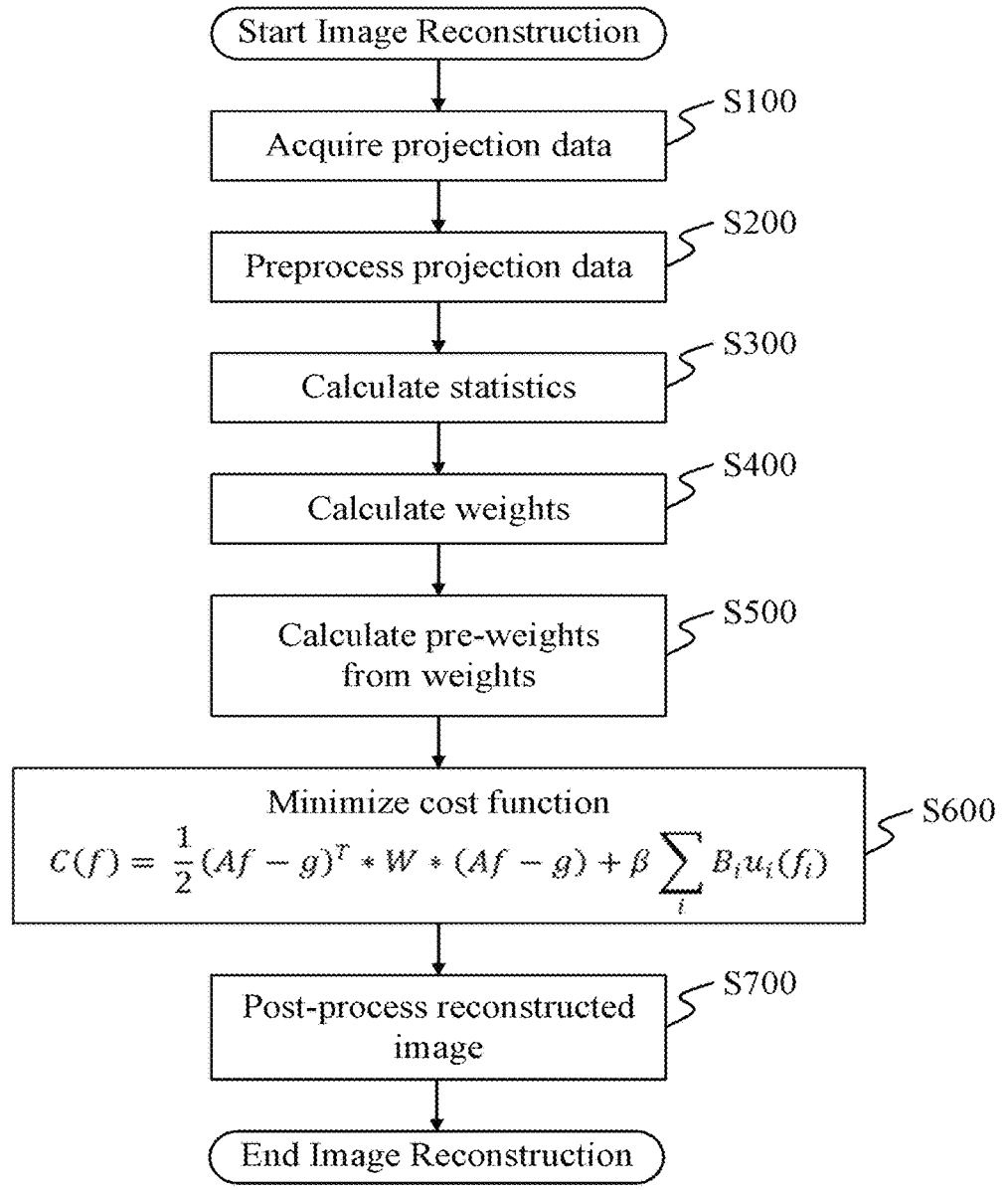
FIG. 2 shows a flowchart of an algorithm for reconstructing a CT image in an exemplary aspect of the disclosure.

FIG. 2 gives an algorithm for image reconstruction according to an aspect of the present disclosure.

In step S100, image projection data is acquired for the CT reconstruction. The projection data includes a plurality of projection data sets, captured with the X-ray tube 101 at a plurality of different locations (views) as the annular frame 102 rotates. The number of the projection data sets should be greater than a number of images required to solve the system Af=g. For example, the number of projection data sets could be 150% of the number required for a solution to the system Af=g.

In step S200, the preprocessing device 106 preprocesses the obtained projection data. The preprocessing can include, for example, sensitivity correction on the raw data, gain and offset corrections for the detector plane, bad pixel replacement, correcting for detector calibrations, detector nonlinearities, polar effects, noise balancing, and material decomposition.

In step S300, the reconstruction device 104 calculates statistics of the projection data sets, which are used to determine the weighting matrix W in the least-squares term of the cost function. The statistics of the projection data sets can be determined, for example, by calculating a variance of each data element in a projection data set over the projection data sets, by calculating a standard deviation of each data element in a projection data set over the projection data sets, or by calculating a covariance matrix of the projection data sets.

In step S400, the reconstruction device 114 calculates the weights according to a desired weighting method from the statistics of the projection data sets calculated in step S300. The calculated weights are the elements of the weighting matrix W. In one weighting method, the reconstruction device 114 calculates the variance of each data element of the detector plane over the projection data sets in step S300, and the weighting matrix W is constructed as a diagonal matrix, with the $i^{th}$ diagonal entry of the matrix being given by $w_i = 1/\sigma_i^2$, where $\sigma_i^2$ is the variance of the $i^{th}$ data element value calculated over the projection data sets.

In step S500, the pre-weights $B_i$ are calculated from the weights determined in step S400. The diagonal of the weighting matrix has a dimensionality equal to that of a projection data set, but the pre-weights $B_i$ have a dimensionality equal to that of a reconstructed image. The forward projection operator is a map from the reconstructed image space to the projection space. The backprojection operator is a map from the projection space to the reconstructed image space, and can be used to associate a set of pre-weights $B_i$ with the weighting matrix elements. The calculation of the pre-weights $B_i$ is given below.

In step S600, the image f that minimizes the cost function C $$C(f) = \frac{1}{2}(Af - g)^T * W * (Af - g) + \beta \sum_i B_i u_i(f_i)$$

is calculated by the reconstruction device 114 using an optimization algorithm. The value of f that minimizes the cost function C can be calculated using any of the conventional optimization algorithms known to one of ordinary skill in the art, for example, the gradient descent algorithm, the Gauss-Seidel algorithm, etc.

In step S700, the reconstruction device 114 post-processes the reconstructed image. Post-reconstruction processing performed by the reconstruction device 114 can include filtering and smoothing the reconstructed image, volume rendering processing, and image difference processing as needed.

The three-dimensional volume image having been reconstructed, the image reconstruction algorithm ends.

Figure 3:
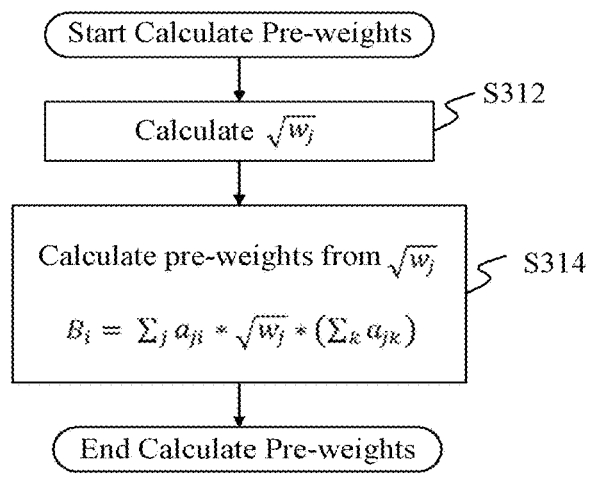
FIG. 3 shows a flowchart of an algorithm for calculating pre-weights in an exemplary aspect of the disclosure.

In FIG. 3, a method for calculating the pre-weights in another embodiment begins in step S312 with calculating the square roots of the diagonal terms $\sqrt{w_j}$ of the weighting matrix W. The diagonal terms of the weighting matrix are positive since they are the reciprocal of a variance which is positive, so this square root can be defined for every $w_j$.

In step S314, the pre-weights $B_i$ are calculated using the expression $B_i = \Sigma_j \alpha_{ji} * \sqrt{w_j} * (\Sigma_k \alpha_{jk})$. The term $\Sigma_k \alpha_{jk}$ in the expression is a sum over the rows of the forward projection operator A, or equivalently a forward projection of a vector of 1s. This sum corresponds to a penetration depth of the X-rays into the object being imaged. After the sum over k, the term $\Sigma_k \alpha_{jk}$ has a remaining dimensionality equal to the dimensionality of the projection image space. This quantity is then multiplied, point by point, by the square root of the diagonal terms $\sqrt{w_j}$ of the weighting matrix W, and backprojected using the backprojection operator to give the pre-weights $B_i$.

Figures 4, 5:
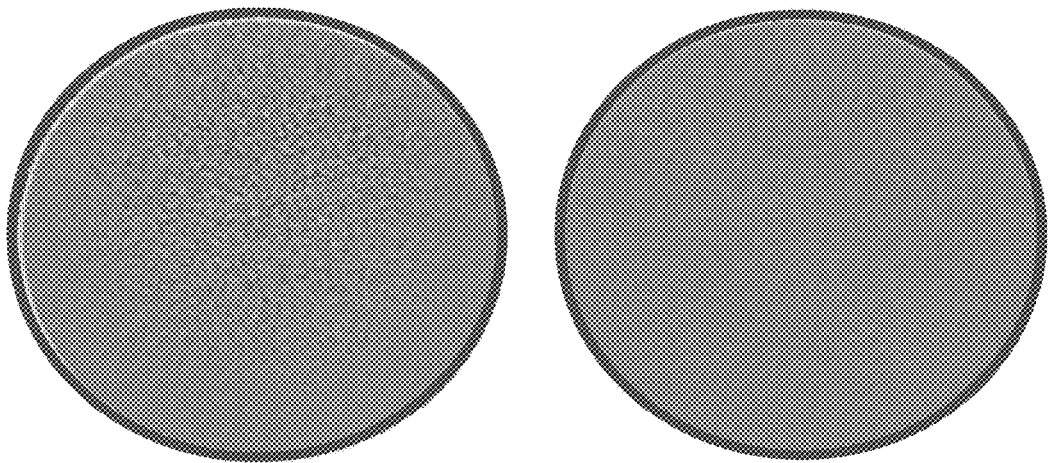
FIG. 4 illustrates a reconstructed image using a penalized weighted least-squares method with uniform pre-weighting factors.
FIG. 5 illustrates a reconstructed image using a penalized weighted least-squares method with pre-weighting factors in an exemplary aspect of the disclosure.

This completes the algorithm for calculation of the pre-weights $B_i$ in one embodiment. FIG. 4 represents an example of a reconstructed CT image of an off-centered water cylinder phantom using the PWLS approach with uniform pre-weighting. FIG. 5 represents an example of a reconstructed CT image of an off-centered water cylinder using the PWLS approach with the pre-weights calculated according to the method of FIG. 3. As shown in FIGS. 4 and 5, the uniformity of the noise distribution is improved.

Figure 6:
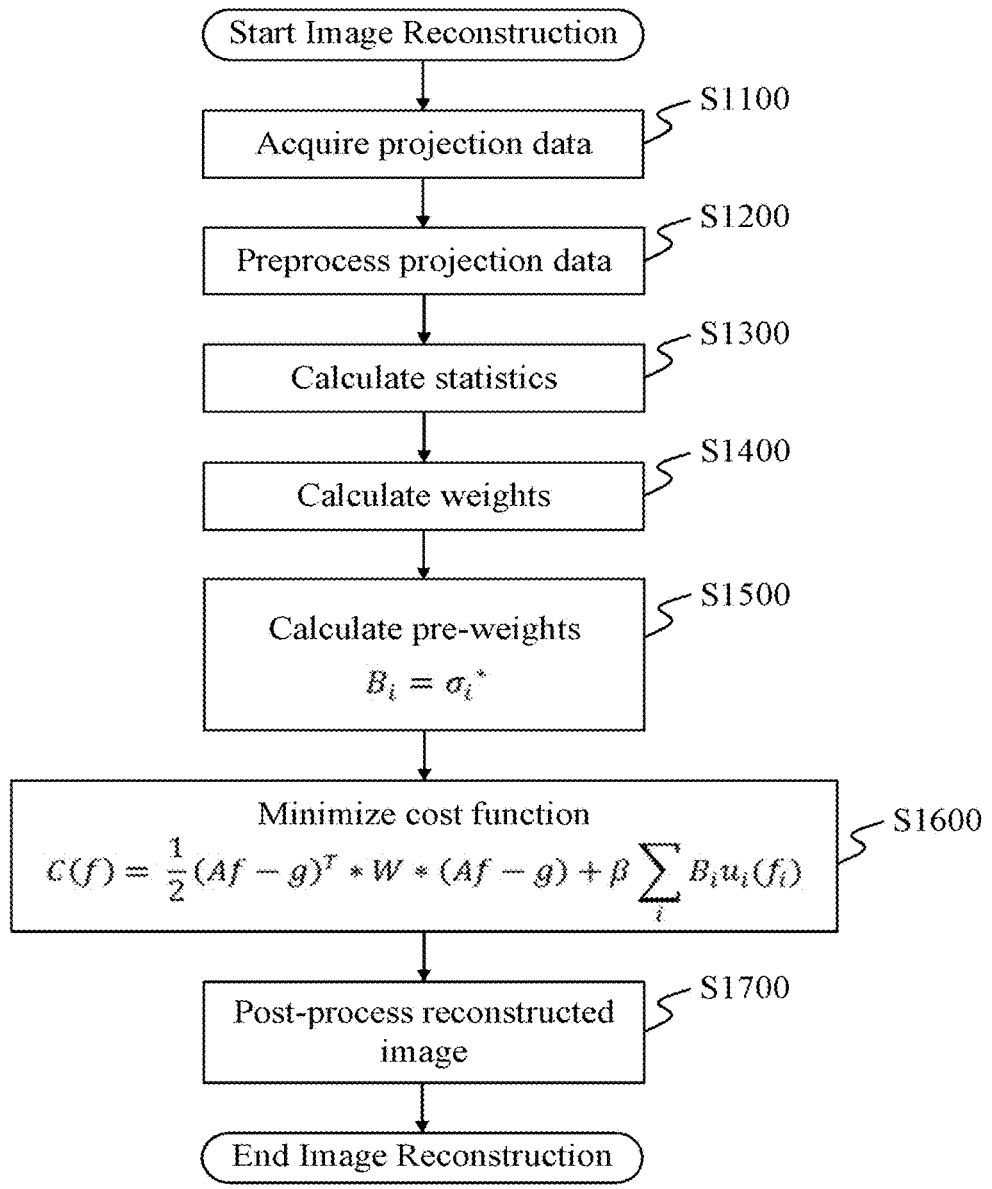
FIG. 6 shows a flowchart of an algorithm for reconstructing a CT image in an exemplary aspect of the disclosure.

FIG. 6 gives an algorithm for image reconstruction according to another embodiment.

In step S1100, image projection data is acquired for the CT reconstruction. The projection data includes a plurality of projection data sets captured with the X-ray tube 101 at a plurality of different locations along the annular frame 102. The number of the projection data sets should be greater than a number of images required to solve the system Af=g. For example, the number of projection data sets can be 150% of the number required for a solution to the system Af=g.

In step S1200, the preprocessing device 106 preprocesses the obtained projection data. The preprocessing can include, for example, sensitivity correction on the raw data, gain and offset corrections for the detector plane, bad pixel replacement, correcting for detector calibrations, detector nonlinearities, polar effects, noise balancing, and material decomposition.

In step S1300, the reconstruction device 104 calculates statistics of the projection data sets, which are used to determine the weighting matrix W in the least-squares term of the cost function. The statistics of the projection data sets can be determined, for example, by calculating a variance of each data element in a projection data set over the projection data sets, by calculating a standard deviation of each data element in a projection data set over the projection data sets, or by calculating a covariance matrix of the projection data sets.

In step S1400, the reconstruction device 114 calculates the weights according to a desired weighting method from the statistics of the projection data sets calculated in step S1300. The calculated weights are the elements of the weighting matrix W. In one weighting method, the reconstruction device 114 calculates the variance of each data element of the detector plane over the projection image sets in step S1300, and the weighting matrix W is constructed as a diagonal matrix, with the $i^{th}$ diagonal entry of the matrix being given by $w_i = 1/\sigma_i^2$, where $\sigma_i^2$ is the variance of the $i^{th}$ data element values calculated over the projection data sets.

In step S1500, the reconstruction device 114 calculates the pre-weights $B_i$ from the variance of the voxels of the image f as reconstructed via filtered backprojection (FBP) algorithms. In one pre-weighting method, the pre-weights are calculated using $B_i = \sigma_i^*$, where $\sigma_i^*$ denotes the square root of the variance of the voxel $f_i$, i.e., the standard deviation of the variance of the voxel $f_i$. The asterisk is used here to differentiate variances $\sigma_i^*$ based on voxels in the image f from variances $\sigma_i$ based on data elements in the projection images.

Several methods for estimating the quantity $\sigma_i^*$ without having to solve for the image f first are available to those of ordinary skill in the art. For example, noise map estimation can be performed by obtaining two correlated view projection data sets, reconstructing two images, and estimating the noise map using the two images.

In step S1600, the image f which minimizes the cost function C $$C(f) = \frac{1}{2}(Af - g)^T * W * (Af - g) + \beta \sum_i B_i u_i(f_i)$$

is calculated by the reconstruction device 114 using an optimization algorithm. The value of f which minimizes the cost function C can be calculated using any of conventional optimization algorithms known to one of ordinary skill in the art, for example, the gradient descent algorithm, the Gauss-Seidel algorithm, and the like.

In step S1700, the reconstruction device 114 post-processes the reconstructed image. Post-reconstruction processing performed by the reconstruction device 114 can include filtering and smoothing the reconstructed image, volume rendering processing, and image difference processing as needed.

The three-dimensional volume image having been reconstructed, the image reconstruction algorithm ends.

While certain embodiments have been described herein, these embodiments are presented by way of example only, and are not intended to limit the scope of the disclosure. Indeed, using the teachings in this disclosure, a person having ordinary skill in the art could modify and adapt the disclosure in a various ways, making omissions, substitutions and changes in the form of the embodiments described herein without departing from the spirit of the disclosure.

Moreover, in interpreting the disclosure, all terms should be interpreted in the broadest possible manner consistent with the context. The accompanying claims and their equivalents are intended to cover such forms or modifications as would fall within the scope and spirit of the disclosure.

For example, the weighting matrix W need not have a diagonal form, but may be given by the inverse of the correlation matrix. In the aspect of the disclosure where the elements of the weighting matrix are used to determine the pre-weights, the pre-weighting coefficients $B_i$ must have the same dimensionality as the volume image space. However, different functions of the weighting matrix elements could be backprojected to give other objects having the required dimensionality. In the aspect of the disclosure where the estimated standard deviation of the volume image voxels are used to determine the pre-weights $B_j$, a different function of the standard deviations could be used.

The invention claimed is:

1. A method for computed tomography (CT) image reconstruction, comprising:
    acquiring a plurality of projection data sets generated by a plurality of detector elements that detect X-ray radiation directed to an object by an X-ray source;
    calculating a set of weights based on the acquired projection data sets;
    calculating a set of pre-weights based on the calculated weights; and
    minimizing a penalized weighted least-squares cost function to produce a reconstructed image, the cost function being a sum of a weighted least-squares term and a penalty term,
    wherein the weighted least-squares term is weighted using the calculated set of weights,
    wherein the penalty term is weighted using the calculated set of pre-weights, and
    wherein the penalty term includes a penalty function defined for each voxel of the reconstructed image.

2. The method according to claim 1, wherein the step of calculating the set of weights includes calculating statistical information from the plurality of projection data sets.

3. The method according to claim 1, wherein the penalty term includes a sum of the penalty function evaluated at each of the voxels of the reconstructed image.

4. The method according to claim 1, wherein
    the step of calculating the set of weights includes calculating elements of a square weighting matrix, and
    the step of calculating the set of pre-weights includes applying a backprojection operator to a product of a function of diagonal elements of the weighting matrix and X-ray penetration terms calculated by summing the rows of a forward projection operator.

5. The method according to claim 4, wherein the function of the diagonal elements of the weighting matrix is a square root of the diagonal elements of the weighting matrix.

6. A method of computed tomography (CT) image reconstruction, comprising:
    acquiring a plurality of projection data sets generated by a plurality of detector elements that detect X-ray radiation directed to an object by an X-ray source;
    calculating a set of weights based on the acquired projection data sets;
    calculating a set of pre-weights based on the projection data sets; and
    minimizing a penalized weighted least-squares cost function to produce a reconstructed image, the cost function being a sum of a weighted least-squares term and a penalty term,
    wherein the weighted least-squares term is weighted using the calculated set of weights,
    wherein the penalty term is weighted using the calculated set of pre-weights, and
    wherein the penalty term includes a penalty function defined for each voxel of the reconstructed image.

7. The method according to claim 6, wherein the step of calculating the set of weights includes calculating statistical information from the plurality of projection data sets.

8. The method according to claim 6, wherein the penalty term includes a sum of the penalty function evaluated at each of the voxels of the reconstructed image.

9. The method according to claim 6, wherein
    the step of calculating the set of weights includes calculating matrix elements of a square weighting matrix,
    the step of calculating the set of pre-weights includes estimating a variance of volume elements of the reconstructed image, and
    the pre-weights are a function of the variance of the volume elements.

10. The method according to claim 9, wherein the pre-weights are a square root of the variance of the volume elements.

11. A computed tomography (CT) apparatus, comprising:
    a radiation source configured to produce radiation directed to an object space;
    a plurality of detector elements configured to detect the radiation produced by the radiation source, the plurality of detector elements being configured to generate projection data;
    a rotation mount configured to rotate the radiation source around the object space, the radiation source being fixedly connected to the rotation mount; and
    processing circuitry configured to
        receive the projection data from the plurality of detector elements, the projection data including a plurality of projection data sets;
        calculate a set of weights based on the received projection data sets;
        calculate a set of pre-weights based on the calculated weights; and
        minimize a penalized weighted least-squares cost function to produce a reconstructed image, the cost function being a sum of a weighted least-squares term and a penalty term,
        wherein the weighted least-squares term is weighted using the calculated set of weights,
        wherein the sum in the penalty term is weighted using the calculated set of pre-weights, and
        wherein the penalty term includes a penalty function defined for each voxel of the reconstructed image.

12. The CT apparatus according to claim 11, wherein the processing circuitry is further configured to calculate the set of weights using statistical information calculated from the plurality of projection data sets.

13. The CT apparatus according to claim 11, wherein the processing circuitry is further configured to calculate the penalty term using a sum of the penalty function evaluated at each of the voxels of the reconstructed image.

14. The CT apparatus according to claim 11, wherein
    the processing circuitry is further configured to
        calculate the set of weights using calculated elements of a square weighting matrix, and
        calculate the set of pre-weights by applying a backprojection operator to a product of a function of diagonal elements of the weighting matrix and X-ray penetration terms calculated by summing the rows of a forward projection operator.

15. The CT apparatus according to claim 14, wherein the function of the diagonal elements of the weighting matrix is a square root of the diagonal elements of the weighting matrix.

* * * * *